(12) United States Patent
Sogaro (10) Patent No.: US 6,719,729 B2
(45) Date of Patent: Apr. 13, 2004

(54) PREFILLED TELESCOPING MULTIPLE CHAMBER AMPOULE DEVICE

(75) Inventor: Alberto C. Sogaro, Kronberg (DE)

(73) Assignee: Dentaco Dentalindustrie und-Marketing GmbH, Bad Homburg (DE)

(*) Notice: Subject to any disclaimer, the term of this patent is extended or adjusted under 35 U.S.C. 154(b) by 66 days.

(21) Appl. No.: 10/010,146

(22) Filed: Nov. 8, 2001

(65) Prior Publication Data

US 2002/0087122 A1 Jul. 4, 2002

(30) Foreign Application Priority Data

Nov. 9, 2000 (DE) ..................... 200 19 091 U (51) Int. Cl.$^7$ .......................... A61M 5/00; A61M 37/00; B67D 5/60
(52) U.S. Cl. ................. 604/191; 604/82; 222/145.5
(58) Field of Search ............... 604/82, 89, 91, 604/181–184, 187, 191, 218, 221, 226, 231, 258; 222/145.1, 145.5, 145.6

(56) References Cited

U.S. PATENT DOCUMENTS

| | | | | |
|---|---|---|---|---|
| 3,563,415 A | * | 2/1971 | Ogle | ................. 222/145.4 |
| 3,722,512 A | * | 3/1973 | Hein et al. | ............... 604/231 |
| 4,657,534 A | * | 4/1987 | Beck et al. | ................ 604/90 |
| 4,741,737 A | * | 5/1988 | Meyer et al. | .............. 604/140 |
| 4,941,876 A | * | 7/1990 | Meyer et al. | ............... 604/89 |
| 5,354,285 A | * | 10/1994 | Mazurik et al. | .......... 604/191 |
| 5,630,800 A | * | 5/1997 | Blank et al. | ................ 604/82 |
| 6,224,568 B1 | * | 5/2001 | Morimoto et al. | ........... 604/89 |

FOREIGN PATENT DOCUMENTS

| | | | | |
|---|---|---|---|---|
| EP | 0111796 | * | 2/1983 | ............ A61M/5/28 |
| EP | 0 111 796 A1 | | 6/1984 | |
| WO | WO 97 20538 A1 | | 6/1997 | |
| WO | WO 98 53789 A1 | | 12/1998 | |
| WO | WO9917833 | * | 4/1999 | ............ A61M/37/00 |

* cited by examiner

Primary Examiner—Brian L. Casler
Assistant Examiner—Catherine S. Williams
(74) Attorney, Agent, or Firm—Quarles & Brady LLP (57) ABSTRACT

A prefilled telescoping multiple chamber ampoule device separately storing at least two different flowable components includes a container and a piston unit. The container has at least two axially extending chambers with circumferential sealing means projecting inwardly from inner walls of the chambers. The piston unit has at least two pistons and a transversely extending mount integrally adjoining forward ends of the pistons. Each piston has a passage axially extending within its interior as well as an outlet opening at a forward end and a transverse inlet opening near a rearward end. The pistons are arranged for coaxial telescoping movement of the container and the piston unit toward one another from a closed storage position into an open release position. In the closed storage position, the rearward ends of the pistons are spaced from the rearward ends of the chambers so as to define therein reservoirs containing one of the components. The circumferential sealing means prevents fluid communication between the reservoirs and the transverse inlet openings of the pistons so as to prevent release of the components from the reservoirs during transportation and storage. In the open release position, the rearward ends of the pistons are moved toward the rearward ends of the chambers whereby the sealing means expose the transverse inlet openings of the passages of the pistons to the reservoirs so as to release the components through the outlet openings of the passages of the pistons as the volumes of the reservoirs are reduced.

27 Claims, 8 Drawing Sheets

PREFILLED TELESCOPING MULTIPLE CHAMBER AMPOULE DEVICE

BACKGROUND OF THE INVENTION

The invention relates to prefilled telescoping multiple chamber ampoule devices separately storing at least two different flowable components. More particularly, the invention relates to prefilled telescoping multiple chamber ampoule devices for dispensing at least two different flowable components which are separately stored in the device. The dispensed components are allowed to intermix with one another after being released and prior to application, or they are kept separately after being released for successive application. The range of application comprises the fields of medicine, chemistry, bio genetics, cosmetics and other fields where it is necessary to store the different components of a multi-component product separately from one another and just mix them with one another immediately prior to application or apply them successively. Furthermore, in these fields of application it is frequently necessary or at least desirable to store the individual components in an air-tight or fluid-tight manner.

International PCT application having the publication number WO 99/17833, published on Apr. 15, 1999, discloses a fibrin sealant cartridge assembly for applying a solution of fibrinogen and a solution of thrombin. The cartridge assembly comprises a container unit having a first and a second container arranged parallel to one another, a piston unit comprising a first and a second piston matingly cooperating with the first and the second container, respectively. Each container stores one of the two solutions. Each piston has a passageway axially extending within the piston through the entire piston. Hence, each passageway has an axial inlet opening which is always in fluid communication with the associated container. Furthermore, each passageway has an axial outlet opening which is in fluid communication with a nozzle attached to the piston. Telescopic movement of the container unit towards the piston unit decreases the volumetric capacity of the containers forcing the solutions therein to flow into the passageways and be dispensed from the nozzles onto an application site. A trip applicator may be attached to the two nozzles for dispensing the two solutions in close proximity to one another. The trip applicator allows a user to spread and/or mix the protein solutions on the application site after they have been dispensed through the outlet openings of the trip applicator. By arranging the outlet openings of the trip applicator very close to each other the solutions intermix before being tripped onto the application site.

In the fibrin sealant cartridge assembly described above, there is a possibility of contaminating the solutions stored in the container as the passageways axially extending through the entire pistons are in continuous fluid communication with the containers. Furthermore, the piston unit consists of several parts including a sealing ring being attached to the outer wall of each piston.

SUMMARY OF THE INVENTION

It is an object of the present invention to provide a prefilled telescoping multiple chamber ampoule device which prevents contamination of individual components contained in the device during transportation and storage, and which has a simple construction, can be assembled in an easy manner and manufactured at low expense for allowing the device to be disposed of after use.

Another object of the invention is to provide a prefilled telescoping multiple chamber ampoule device which avoids an unintentional release or dispense of the components stored in the device.

Another object of the invention is to provide a prefilled telescoping multiple chamber ampoule device which offers the possibility of adapting it to various application purposes without changing the basic design.

Another object of the invention is to provide a novel piston unit for use in a prefilled telescoping multiple chamber ampoule device.

These and other objects are accomplished by providing a novel prefilled telescoping multiple chamber ampoule device separately storing at least two different flowable components. The ampoule device comprises a container having at least two axially extending chambers which are arranged in parallel to one another. Each chamber has a closed rearward end and an open forward end. An integrally formed circumferential sealing means projects inwardly from the inner wall of each chamber. In addition, the ampoule device comprises a piston unit having at least two pistons. A transversely extending mount integrally adjoins the forward ends of the pistons. Each piston has a passage which axially extends within the interior of the piston. The passage has an axial outlet opening at a forward end of the piston and a transverse inlet opening near a rearward end of the piston. Each piston is aligned with one of said chambers and, with its rearward end ahead, is inserted into the open forward end of the chamber and matingly arranged therein for coaxial telescoping movement of the container and the piston unit towards one another from a closed storage position into an open release position. In the closed storage position the rearward end of each piston is spaced a distance from the rearward end of the respective chamber so as to define therein a reservoir containing one of the flowable components. Furthermore, in the closed storage position the circumferential sealing means is sealingly pressed into circumferential contact with the outer wall of the piston at a location so as to prevent fluid communication between the reservoir and the transverse inlet opening of the passage of the piston. Thereby, release of the component from the reservoir into the transverse inlet opening of the passage is prevented in the closed storage position. After initial and during telescoping movement into the open release position, the rearward ends of the pistons are moved towards the rearward ends of the chambers whereby the sealing means expose the transverse inlet openings of passages of the pistons to the reservoirs. Thereby, the components stored in the reservoirs are released through the outlet openings of the passages of the pistons as the volumes of the reservoirs are reduced. Furthermore, after initial telescoping movement the sealing means come into sealing contact with the outer walls of the pistons at a location between the transverse inlet openings and the forward ends of the pistons. Thereby, escape of the components from the reservoirs to the open forward ends of the chambers is prevented.

Preferably, the circumferential sealing means is a sealing lip which, in the closed storage position, is in sealing contact with the outer wall of the piston at a location between the rearward end and the transverse inlet opening of the piston. Optionally, an additional sealing lip is provided which is axially spaced from the first mentioned sealing lip in forward direction. The additional sealing lip assists frictional holding in the closed storage position and guidance during telescoping movement.

In order to provide a multi component dispensing system featuring mixing of the released components, in a preferred embodiment of the invention, the piston unit has a collection and mixing compartment integrally formed on top of the forward ends of the pistons. The collection and mixing compartment is in fluid communication with each one of the outlet openings of the passages of the pistons for simultaneously receiving each one of the released components during telescoping movement.

In order to provide a multi component dispensing system featuring separate and successive application of the released components, in a preferred embodiment of the invention, the piston unit has at least two separate compartments integrally formed on top of the forward ends of the pistons. The compartments extend in axial direction and are arranged in parallel to one another. Each compartment is in fluid communication with only one of the outlet openings of the longitudinal passages of the pistons for separately receiving only one of the released components during telescoping movement. The compartments have open forward ends which may be provided with a common or, alternatively, individual closure means. The closure means may be provided with applicator means.

A novel piston unit for use in a prefilled telescoping multiple chamber ampoule device comprising a container having at least two axially extending chambers arranged in parallel to one another, comprises at least two pistons having forward ends which are integrally connected with one another. Each piston has a passage which axially extends within the interior of the piston. Each piston is aligned with one of the chambers and matingly arranged therein for coaxial telescoping movement of the container and the piston unit towards one another. According to an aspect of the invention, the piston unit has a collection and mixing compartment integrally formed on top of the integrally connected forward ends of the pistons. The compartment is in fluid communication with each one of the outlet openings of the passages of the pistons for simultaneously receiving components released from the container during telescoping movement. According to another aspect of the invention, the piston unit has at least two separate compartments integrally formed on top of the forward ends of the pistons. The compartments extend in axial direction and are arranged in parallel to one another. Each compartment is in fluid communication with only one of the outlet openings of the longitudinal passages of the pistons for separately receiving only one of the released components during telescoping movement.

Alternatively, each compartment is in fluid communication with two outlet openings of the longitudinal passages of the piston. Another alternative is that one compartment of the at least two compartments is in fluid communication with two or even more outlet openings of the longitudinal passages and another compartment is in fluid communication with a different number of outlet openings, for example, only one outlet opening.

The compartments have open forward ends which may be provided with a common or, alternatively, individual closure means. The closure means may be provided with applicator means.

According to a further development of the invention, the one or more of the compartments formed on top of the pistons may also be prefilled with a component.

DETAILED DESCRIPTION OF PREFERRED EMBODIMENTS

Figure 1:
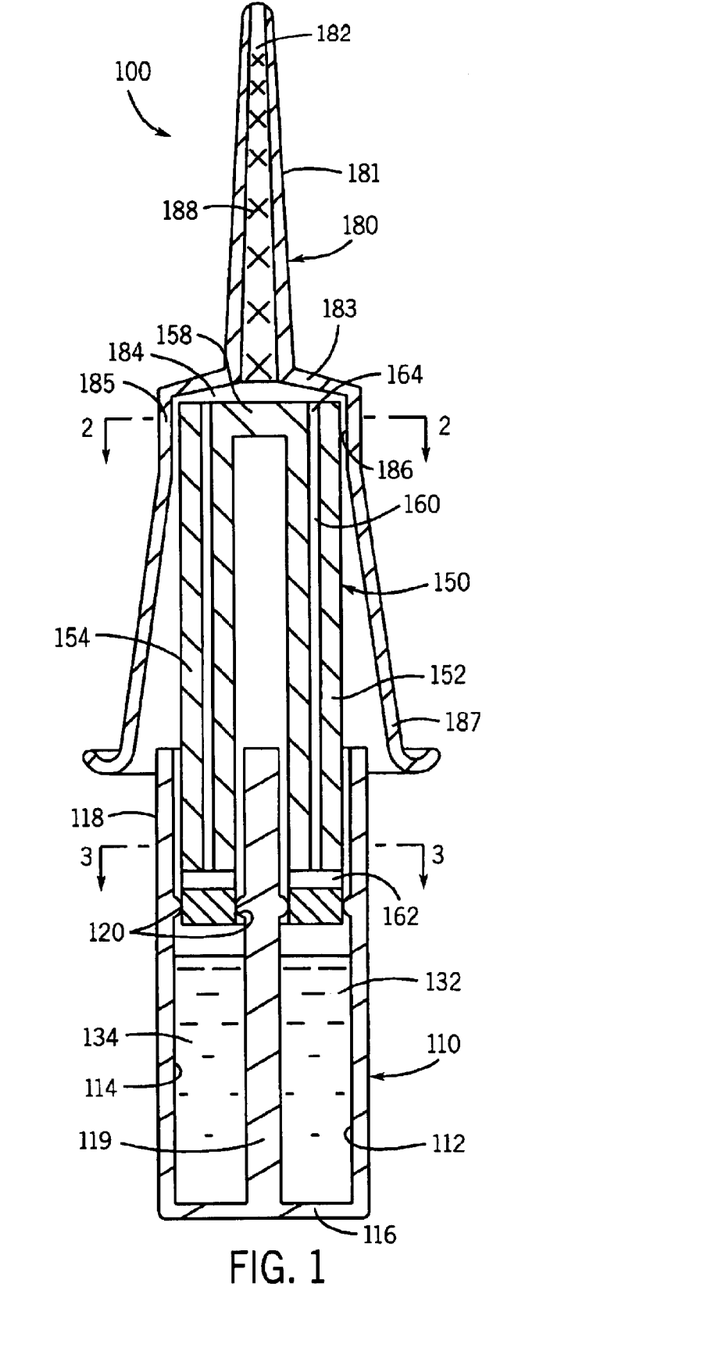
FIG. 1 is a longitudinal sectional view of a first embodiment of a prefilled telescoping multiple chamber ampoule device of the present invention showing the device in a closed storage position.
Figure 2:
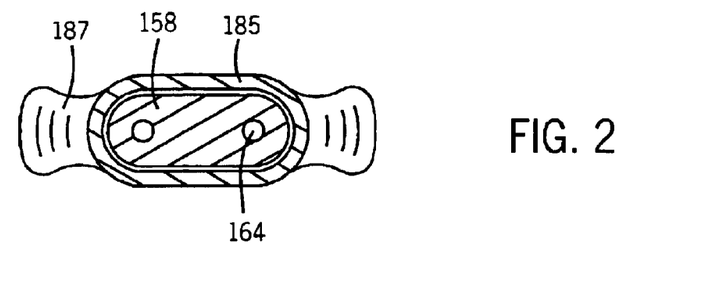
FIG. 2 is a transverse sectional view of the first embodiment along line II—II in FIG. 1.
Figure 3:
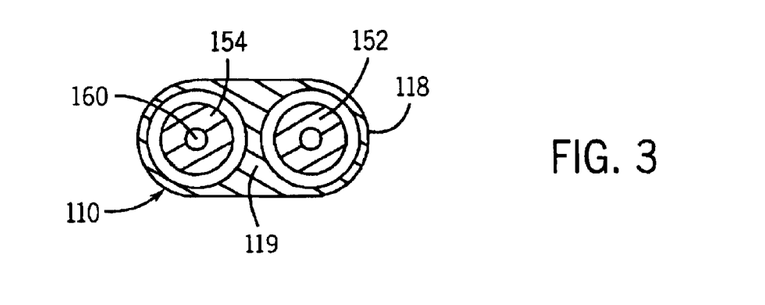
FIG. 3 is another transverse sectional view of the first embodiment along line III—III in FIG. 1.

Referring to FIGS. 1 to 3, a prefilled telescoping multiple chamber ampoule device 100 according to a first embodiment of the present invention comprises a container 110 and a piston unit 150.

The container 110 includes two separate cylindrical chambers 112 and 114. The chambers 112 and 114 extend in a longitudinal or axial direction of the container 110 and are arranged in parallel to one another. The rearward ends of the chambers 112 and 114 are closed by a bottom wall 116 of the container 110. The forward ends of the containers 112 and 114 are open in axial direction. The chambers 112 and 114 are surrounded by an outer wall 118 of the container 110 and separated from one another by a partition 119. Each one of the chambers 112 and 114 is provided with an annular peripheral sealing lip 120 projecting radially inwardly from the inner wall of each chamber between the rearward bottom wall 116 and the forward open end of the chambers.

In a preferred embodiment, the portion 119 may be reduced to a rather narrow connecting strip. Alternatively, each one of the chambers 112 and 114 may be defined by a tubular member having an open forward end and a closed rearward end. The tubular members are spaced from one another and are connected with one another, for example, only at the open forward ends or the closed rearward ends to form an integrated multiple chamber container. These modifications apply to each one of the embodiments disclosed herein.

The piston unit 150 consists of two cylindrical plungers or pistons 152 and 154. The two pistons extend in parallel to one another and are spaced from one another by a distance. The forward ends of the pistons 152 and 154 are integrally connected to one another by means an integrally formed connecting member such as a plate 158. Each one of the pistons 152 and 154 has a longitudinal passage 160 which axially extends within the interior of the piston. The passage 160 has an axial outlet opening 164 to the exterior of the piston unit 150 at the forward end of the piston. Furthermore, the passage 160 has a transverse inlet opening 162 from the exterior of the piston unit 150 near the rearward end of the piston. The piston unit 150 and the container 110 are designed in such a manner that the pistons 152 and 154 can be brought in axial alignment with the chambers 112 and 114 and can be matingly arranged therein for coaxial telescopic movement of the container 110 and the piston unit 150 towards one another.

Depending on the application, an applicator such as a nozzle applicator 180 may be provided. The nozzle applicator 180 consists of a forward portion 181 and a rearward portion 185. The forward portion 181 has a tapered tubular shape and surrounds an outlet channel 182 having a relatively small transverse cross-sectional area. The rearward portion 185 defines an inside space 186 which has an open rearward end and a larger transverse cross-sectional area, the dimensions of which match with the outer dimensions of the transverse cross-sectional are of the forward end of the piston unit 150. In other words, the forward end of the piston unit 150 can be inserted into the inside space 186 of the rearward portion 185 in a fluid-tight manner. The nozzle applicator 180 has a sloping shoulder 183 between the forward portion 181 and the rearward portion 185. The sloping shoulder 183 defines on its inside a flat, truncated compartment 184 adjoining the inside space 186 and the output channel 182. Preferably, a static mixer 188 is inserted in the outlet channel 182 which has an increasingly smaller diameter from its rearward end to its forward outlet end.

FIG. 1 shows the prefilled telescoping multiple chamber ampoule device 100 in a closed storage position. In the closed storage position the rearward ends of the pistons 152 and 154 are inserted into the open forward ends of the chambers 132 and 134 so that the rearward end of each piston is spaced a distance from the bottom of each one of the chambers 112 and 114 defining therein a reservoir. The reservoir defined in the chamber 112 contains a first flowable component 132, and the reservoir defined in the chamber 114 contains a second flowable component 134. In the closed storage position the peripheral sealing lips 120 are fluid-tightly pressed into circumferential contact with the outer walls of the pistons 152 and 154 at a location above the rearward end of each piston and below the transverse inlet opening 162 of the passage 160 within each piston so as to prevent release of the components 132 and 134 from the reservoirs into the transverse inlet openings 162 and to frictionally hold the piston unit 150 in place within the container 110 during storage and transportation.

The nozzle applicator 180 may be provided separately from the prefilled sub-assembly of the device 100 which consists only of two basic parts, i.e. the container 110 and the piston unit 150. However, preferably, the nozzle applicator 180 is already attached to the piston unit 150 in the closed storage position, as shown in FIG. 1.

Prior to activation of the prefilled ampoule device 100 the nozzle applicator 180 has to be attached to the forward end of the piston unit 150, unless done before, for example, prior to enclosing the components 132 and 134 within the container 110 by inserting the rearward ends of the pistons of the piston unit 150. Starting from the closed storage position shown in FIG. 1, the prefilled ampoule device 100 can be telescopically moved into an open release position by manually applying an axial compression force to the axially opposite parts of the device, i.e. the container 110 and the nozzle applicator 180. Accordingly, the nozzle applicator 180 and the container 110 have also the functions of manipulating parts. More specifically, the sloping shoulder 183 offers an engaging surface for one or two fingers of one hand and the bottom wall 116 of the container 110 offers an engaging surface for another finger of the same hand to telescopically move the piston unit 150 and the container 110 towards one another into the open release position.

At the start of telescoping movement the transverse openings 162 ride over the sealing lips 120 and positive pressure is created within the reservoirs of the chambers 112 and 114 containing the components 132 and 134. Accordingly, the components 132 and 134 enter into the transverse inlet openings 162 and are pressed in forward direction through the longitudinal channels 160 of the pistons 152 and 154 into the mixing compartment 184 and from there through the outlet channel 182 to the outside of the device. In the compartment 184 and the outlet channel 182 the two components are intermixed before being sprayed out of the outlet opening of the outlet channel 182. Preferably, the intermixing of the two components is enhanced by means of a static mixer 188 provided within the outlet channel 182.

During axial telescoping movement from the closed storage position, shown in FIG. 1, to the open release position the sealing lips 120 are fluid-tightly pressed into circumferential sliding contact with the outer walls of the pistons 152 and 154 at a location between the transverse openings 162 and the forward end of the piston unit 150 so as to prevent escape of the components 132 and 134 from the reservoirs within the chambers 112 and 114 to the forward open end of the container 110.

In this context, according to the invention, the container 110 is molded from an elastomeric material or any other appropriate material having elastic characteristics, while the piston unit 150 can be molded from a similar material or a relatively rigid plastic material. In a preferred embodiment both parts 110 and 150 are made from polyethylene (PE). Generally, the materials and dimensions of both parts 110 and 150 are preferably chosen such that the container 110 in its entirety is more elastic than the piston unit 150. The piston unit 150 can even be rigid, whereas the container 110 should have a certain degree of elasticity to allow both the sealing engagement between the sealing lips 120 and the outer walls of the pistons 152 and 154 and the telescopic movement between the two parts 110 and 150. With regard to the dimensions of the two parts 110 and 150, in the disassembled state, the outer diameters of the pistons 152 and 154 are larger than the inner diameters of the protruding sealing lips 120 and as large or almost as large as the inner diameters of the chambers 112 and 114, while in the assembled state the circumferential parts of the peripheral walls of the cylindrical chambers 112 and 114 maybe slightly expanded radially outwards at and in axial zones near the sealing lips 120 which are continuously in sealing contact with the outer walls of the pistons 152 and 154. Accordingly, circumferential parts of the peripheral walls of the chambers 112 and 114 are radially elastically expanded together with circumferential parts of the sealing lips 120 such that the sealing lips 120 are expanded to the outer diameters of the pistons 152 and 154. Additionally or alternatively, the sealing lips 120 may be deformed. Of course, the overall design is such that during the axial telescoping movement there are adequate radial spaces or clearances between the inner walls of the chambers 112 and 114 and the outer walls of the pistons 152 and 154 at and near the rearward ends of the pistons 152 and 154 so that the flowable components 132 and 134 contained in the reservoirs of the chambers 112 and 114 can be driven into the transverse inlet openings 162. These considerations apply to each one of the embodiments disclosed herein.

During telescoping movement and dispense of the mixture from the outlet opening of the output channel 182 a relatively high pressure may built up within the flat conically shaped mixing chamber 184. In order to avoid that the forward end of the piston unit 150 inserted into the inside space 186 of the spray or nozzle applicator 180 will be pushed out of the rearward end of the applicator 180 adequate connecting means should be provided between the applicator 180 and the piston unit 150, such as press fit, snap on and similar fastening means, well known in the art. In some applications it may be sufficient to provide the inner wall of the rearward portion 185 or the outer wall of the forward end of the piston unit 150 with an integrally formed frictional and sealing lip transversely extending inwardly or outwardly, respectively.

Furthermore, integrally formed gripping means 187 may be provided on the applicator 180 for the purpose of better handling during telescoping movement.

Other alternative means for improving the manual manipulation of the device for telescoping movement are well known in the art, for example, in the form of transverse protrusions extending from the container 150 or the applicator 180.

In this context, according to the invention, the applicator 180 is molded from an elastomeric material or any other appropriate material having elastic characteristics.

Figure 4:
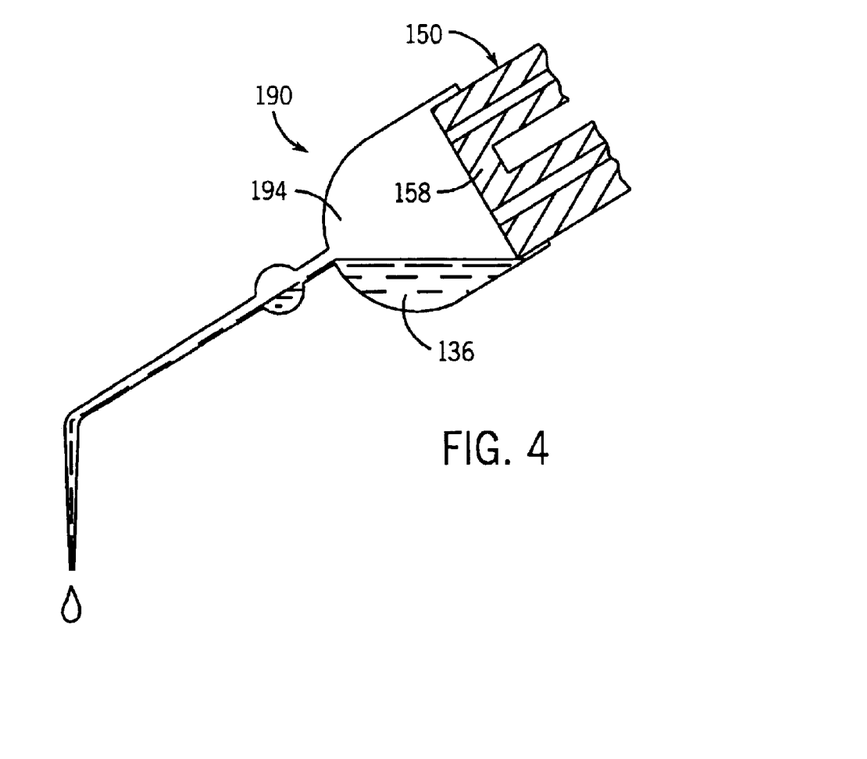
FIG. 4 is a longitudinal sectional view of a forward portion of the first embodiment utilizing another type of applicator and showing the device after release of the components.

With reference to FIG. 4, it should be noted that a variety of applicators may be used in replacement of the spray or nozzle applicator 180. For example, FIG. 4 discloses a dropper applicator 190 the rearward end of which has been attached to the forward end of the piston unit 150. The dropper applicator 190 provides a relatively large mixing compartment 194 for receiving a mixture 136 consisting of the entire volumes of the two components 132 and 134 after the prefilled ampoule device has been fully moved in the open release position in which the rearward ends of the pistons 152 and 154 are close to or in contact with the bottom wall 116 of the container 110.

Figure 5:
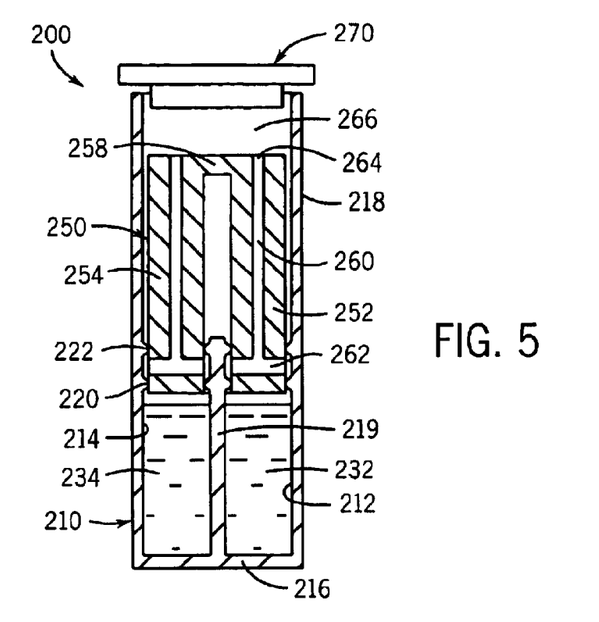
FIG. 5 is a longitudinal sectional view of a second embodiment of a prefilled telescoping multiple chamber ampoule device of the present invention showing the device in a closed storage position.
Figure 6:
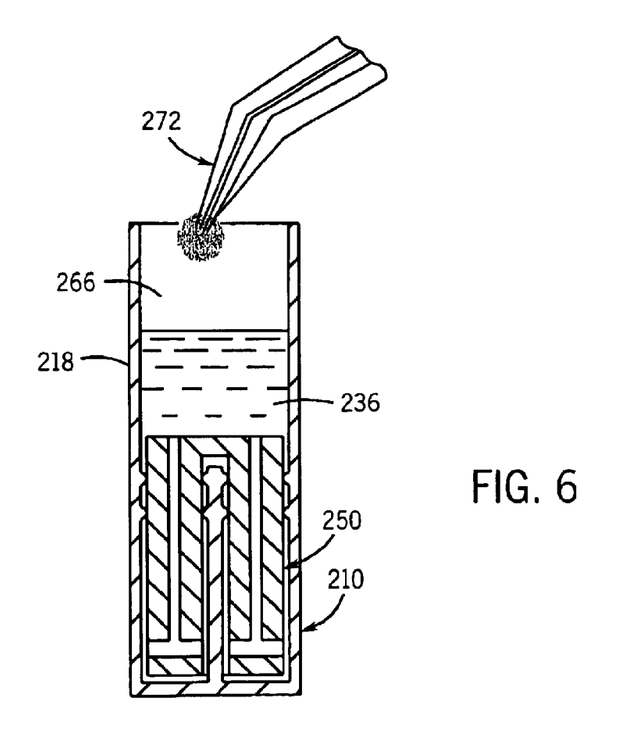
FIG. 6 is a longitudinal sectional view of the second embodiment showing the device in an open release position together with an applicator.

Referring to FIGS. 5 and 6, a prefilled telescoping multiple chamber ampoule device 200 according to a second embodiment of the present invention comprises a container 210 and a piston unit 250. Preferably, a closure means may be provided such as a removable cap 270.

The container 210 has a construction similar to that of the container 110 and includes two separate cylindrical chambers 212 and 214, a bottom wall 216, an outer wall 218 having a rearward portion which surrounds the chambers 212 and 214, a partition 219 separating the chambers 212 and 214 from one another, and an annular peripheral sealing lip 220 projecting radially inwardly from the inner wall of each chamber.

The container 210 is modified with respect to the container 110 insofar as the outer wall 218 has a forward portion that extends in the forward direction beyond the forward ends of the cylindrical chambers 212 and 214 and the partition 219. In addition, the container 210 is provided with a further integrally formed annular sealing lip 222 projecting radially inwardly from the inner wall of each chamber. The annular peripheral sealing lip 222 is spaced by a short distance in the forward direction from the sealing lip 220, as it can be seen from FIGS. 5 and 6.

The piston unit 250 has a construction that is more or less identical to the construction of the piston unit 150 and consists of two plungers or pistons 252 and 254, a connecting plate 258, a longitudinal channel 260 within each piston having a transverse inlet opening 262 and an axial outlet opening 264.

FIG. 5 shows the prefilled telescoping ampoule device 200 in the closed shipping or storage position. As it can be seen, the forward portion of the outer wall 218 of the container 210 defines an inner space for entirely receiving the piston unit 250 in the closed storage position. Accordingly, a closure means or cover such as the cap 270 can be provided on top of the forward end of the container 210.

In the closed storage position, shown in FIG. 5, the rearward ends of the pistons 252 and 254 define within the chambers 212 and 214 reservoirs containing a first flowable substance 232 and a second flowable substance 234. In the closed storage position, the sealing lips 220 and 222 are in fluid-tight contact with the outer walls of the pistons 252 and 254 and are axially located on both sides of the inlet opening 262. It should be appreciated that the sealing lips 222 are optional. They may improve the sealing function and the frictional function maintaining the piston unit 250 in the closed storage position during transportation and storage. The optional provision of a further sealing lip such as sealing lip 222 applies to each one of the embodiments disclosed herein.

For activation of the prefilled ampoule device 200 and telescopical movement of the piston 250 and the container 210 towards one another, the cap 270 is removed and pressure is applied upon the forward face of the piston unit 250 by means of a tool, such as an immerging or dipping applicator 272, while the container 250 is held in hand or standing on a base, such as a table. Alternatively, a rod like extension (not shown) is integrally formed on top of the forward end of the piston unit 150 axially extending in the forward direction for manually activating the ampoule device. The rod like extension may protrude through an opening of the cap 270 to the outside of the device.

FIG. 6 shows the prefilled ampoule device 200 in the fully open release position in which the two substances 232 and 234 are separately released via the longitudinal channels 260 into a mixing compartment defined by the forward end of the piston unit 250 and the inner surface of the forward portion of the outer wall 218 of the container 210. Accordingly, the mixing compartment contains a mixture 236 of the two dispensed components 232 and 234. The mixture 236 can be applied by means of the dipping applicator 272 which can be immerged into the mixture 236 via the open forward end of the container 210.

Figure 7:
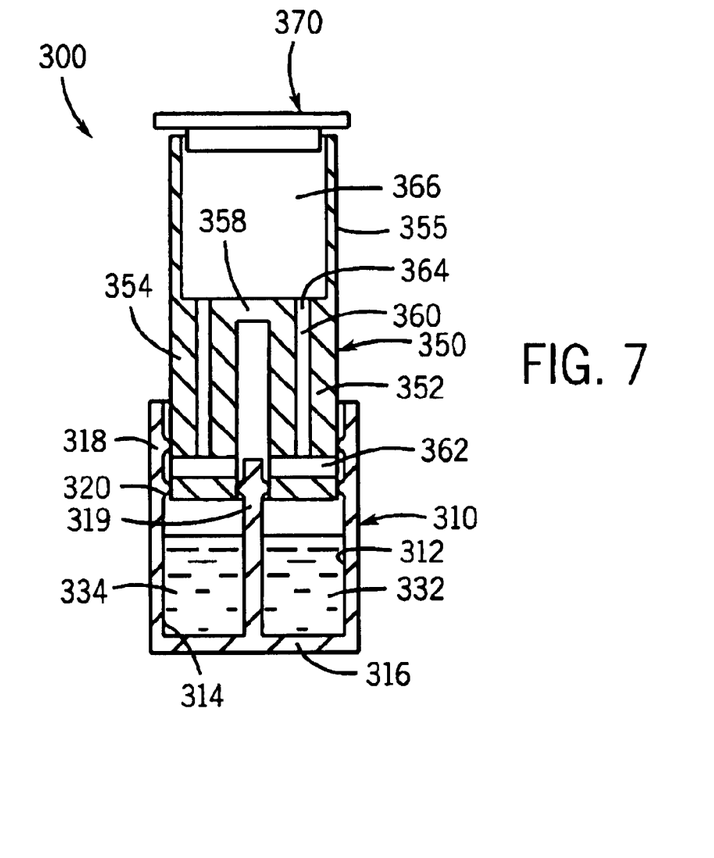
FIG. 7 is a longitudinal sectional view of a third embodiment of a prefilled telescoping multiple chamber ampoule device of the present invention showing the device in a closed storage position.
Figure 8:
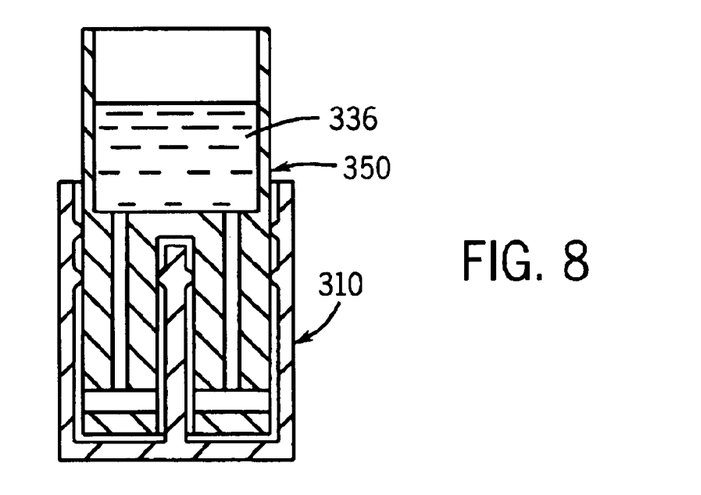
FIG. 8 is a longitudinal sectional view of the third embodiment showing the device in an open release position.

Referring to FIGS. 7 and 8, a prefilled telescoping multiple chamber ampoule device 300 according to a third embodiment of the present invention comprises a container 310 and a piston unit 350 and may be provided with a closure means or cover such as a cap 370.

The construction of the container 310 essentially corresponds to the construction of the container 110. Accordingly, the container 310 includes two separate cylindrical chambers 312 and 314, a bottom wall 316, a surrounding outer wall 318, a partition 319 and an annular peripheral sealing lip 320 projecting radially inwardly from the inner wall of each chamber.

The piston unit 350 has a construction that corresponds essentially to that of the piston unit 150. Accordingly, the piston unit 350 consists of two pistons 352 and 354, a plate 358 connecting the forward ends of the pistons together, a longitudinal channel 360 extending within each piston and having a transverse inlet opening 362 and an axial outlet opening 364. In addition to the piston units 150 and 250, the piston unit 350 has an integrally formed mixing compartment 366 on top of the forward ends of the pistons 352 and 354. As it can be seen from FIG. 7, the mixing compartment 366 is peripherally surrounded by an outer wall 355 axially extending in forward direction from the forward ends of the pistons 352 and 354. The connecting plate 358 defines the bottom of the mixing compartment 366 and the outlet openings 364 of the longitudinal channels 360 are in fluid communication with the mixing compartment 366. The mixing compartment 366 has an open forward end. FIG. 7 shows the prefilled telescoping ampoule device 300 in the closed storage position in which a first flowable component 332 and a second flowable component 334 are contained and enclosed in the reservoirs of the chambers 312 and 314. The forward open end of the mixing chamber 366 may be provided with a removable closure means or cover such as the cap 370.

FIG. 8 shows the prefilled telescoping ampoule device 300 in the fully open release position after telescoping movement. In the fully open release position the two components 332 and 334 have been separately released through the longitudinal channels 360 into the mixing compartment 366 which now contains a mixture 336 of the two released components 332 and 334. After having removed the cap 370 the mixture 336 can be applied by an applicator such as the applicator 272 shown in FIG. 6.

Figure 9:
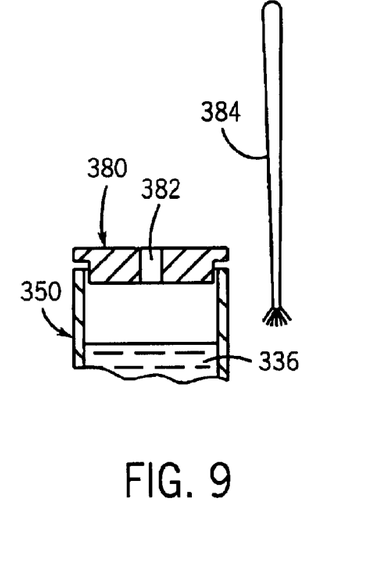
FIG. 9 is a longitudinal sectional view of a forward portion of the third embodiment showing the device after release of the components together with another type of applicator.

FIG. 9 shows a modified closure means in form of a cap 380 having a through hole 382. The through hole 382 allows the insertion of a separately provided applicator tool 384 for immersion into the mixture 336.

Figure 10:
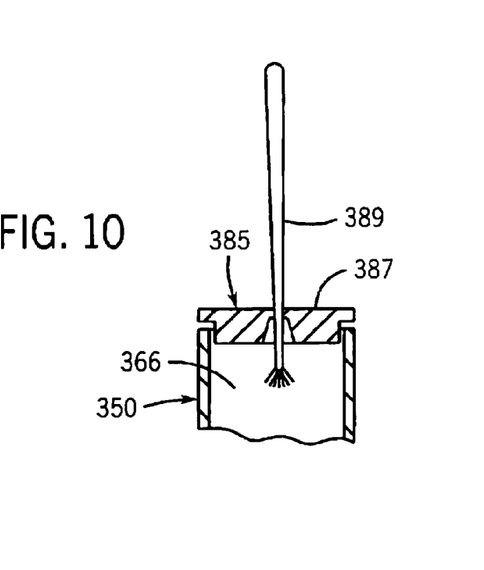
FIG. 10 is a longitudinal sectional view of a forward portion of the third embodiment showing a similar type of applicator prior to release of the components.

FIG. 10 shows another modified closure means in form of a cap 385. An applicator tool 389 extends through the cap into the mixing compartment 366. The applicator tool 389 is fluid-tightly connected to the cap 385 by a membrane 387 or the like. For activating the prefilled telescoping ampoule device 300 and starting telescoping movement, the applicator tool 389 is rotated in order to rupture the membrane 387. The applicator tool 389 is now free to be pushed deeper into the mixing compartment 366 until it comes into contact with the forward end face of the plate 358 or the pistons 352 and 354 and then, pushes the piston unit 350 into the container 310 for axial telescoping movement. Thereby the components 332 and 334 are released through the longitudinal channels 360 into the mixing compartment 366.

Alternatively, for telescoping movement manual pressure is applied to the cap 385 and container 310. Thereafter, the applicator tool 389 is freed from the membrane 387 and the cap 385.

Figure 11:
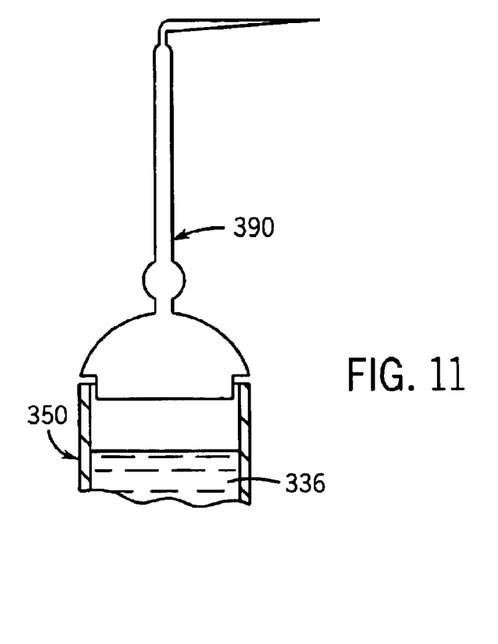
FIG. 11 is a longitudinal sectional view of the third embodiment showing the device after release of the components together with a further type of applicator.

As shown in FIG. 11, other applicator means such as a dropper applicator 390 may be attached to the open forward end of the mixing compartment 366 in order to dispense the mixture 336 in form of single droplets as it can be seen for example in FIG. 4.

Referring to FIGS. 12 to 16, a prefilled telescoping multiple chamber ampoule device 400 according to a fourth embodiment of the present invention comprises an integrally formed container 410 and an integrally formed piston unit 450.

Figure 12:
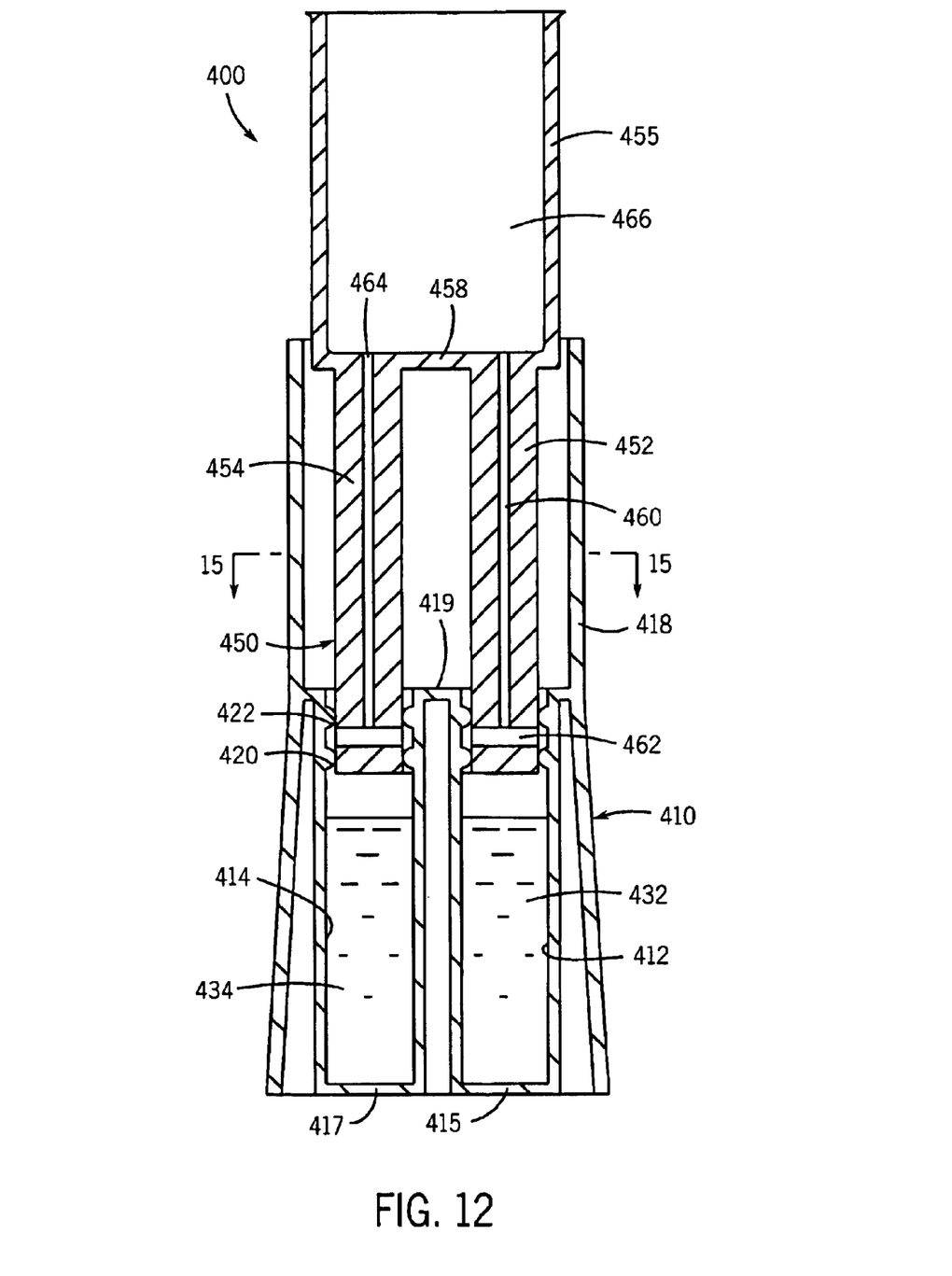
FIG. 12 is a longitudinal sectional view of a fourth embodiment of a prefilled telescoping multiple chamber ampoule device of the present invention showing the device in a closed storage position.
Figure 13:
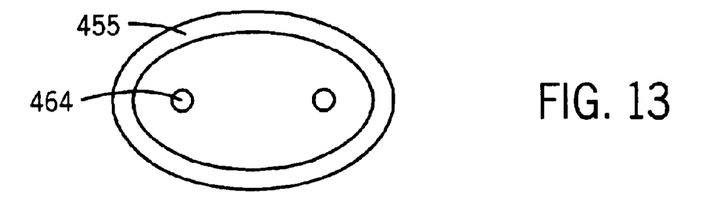
FIG. 13 is a top plan view of a piston unit of the fourth embodiment.
Figure 14:
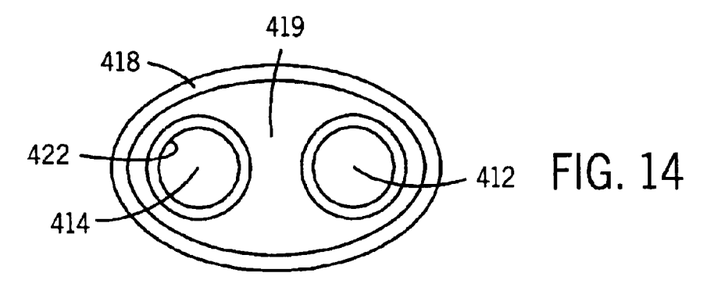
FIG. 14 is a top plan view of a container of the fourth embodiment.
Figure 15:
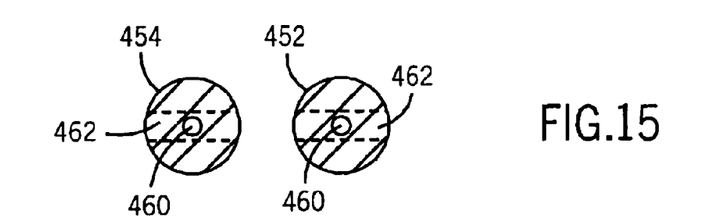
FIG. 15 is a transverse sectional view of the piston unit of the fourth embodiment along line XV—XV in FIG. 12.
Figure 16:
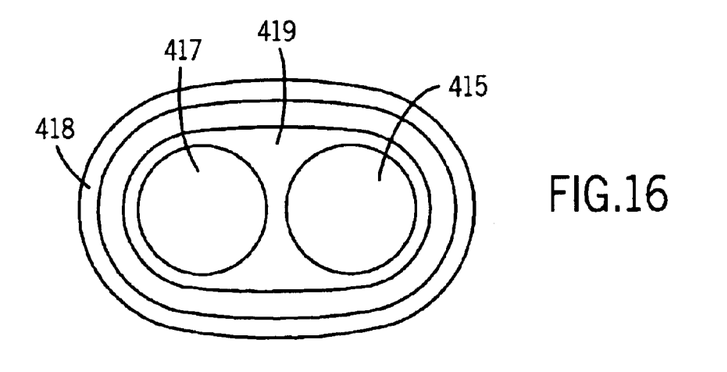
FIG. 16 is a bottom plan view of the container of the fourth embodiment.

The container 410 includes two separate cylindrical chambers 412 and 414. Each one of the chambers 412 and 414 is circumferentially surrounded by the side wall of a tubular portion of the container 450. The rearward ends of the tubular portions are closed by bottom walls 415 and 417. The open forward ends of the tubular portions are integrally connected with one another by a plate-like portion 419 supporting the tubular portions and leaving the chambers 412 and 414 open in forward direction. Referring to FIGS. 14 and 16, the plate-like portion 419 has an essentially oval cross-sectional area. Referring to FIGS. 12, 13, and 16, the tubular portions defining the chambers 412 and 414 are arranged in parallel to one another and are spaced from one another.

The plate-like portion 419 transversely extends beyond the outer walls of the tubular portions. The peripheral side wall of the plate-like portion 419 is integrally connected to an outer wall 418 of the container 450. A forward portion of the outer wall 418 axially extends from the plate-like portion 419 in forward direction. Referring to FIGS. 12 and 13, the forward portion of the outer wall 418 surrounds a space which has an open forward end and an essentially oval cross-sectional area.

A rearward portion of the outer wall 418 axially extends from the plate-like portion 418 in the rearward direction. The rearward portion of the outer wall 418 surrounds the tubular portions and is spaced therefrom in transverse direction. The rearward end of the outer wall 418 and the bottom walls 415 and 417 of the tubular portions are flush with one another.

Referring to FIG. 12, each one of the chambers 412 and 414 is provided with an annular peripheral sealing lip 420 projecting radially inwardly from the inner wall of each chamber at a location spaced by a distance from the plate-like portion 419. Optionally, each one of the chambers 412 and 414 is provided with a further annular peripheral sealing lip 422 projecting radially inwardly from the inner wall of each chamber at a location between the sealing lip 420 and the plate-like portion 419.

The piston unit 450 consists of two cylindrical plungers or pistons 452 and 454. The two pistons extend in parallel to one another and are spaced from one another by a distance. The forward ends of the pistons 452 and 454 are integrally connected to one another by means of an integrally formed connecting member such as a plate 458. Each one of the pistons 452 and 454 has a longitudinal passage 460 which axially extends within the interior of the piston. The passage 460 has an axial outlet opening 464 at the forward end of the piston. Furthermore, the passage 460 has a transverse inlet opening 462 near the rearward end of the piston.

The piston unit 450 has an integrally formed collecting and mixing compartment 466 on top of the forward ends of the pistons 452 and 454. Referring to FIGS. 12 and 13, the compartment 466 is peripherally surrounded by an outer wall 455 axially extending in forward direction from the forward surface of the plate 458. The connecting plate 458 defines the bottom of the mixing compartment 466 and transversely extends beyond the outer walls of the pistons 452 and 454. The outlet openings 464 of the longitudinal passages or channels 460 are in fluid communication with the compartment 466. Referring to FIG. 13, the outer wall 455 of the compartment 466 has an essentially oval outer contour in the transverse direction corresponding to the inner contour of the forward portion of the outer wall 418 of the container 410.

The piston unit 450 and the container 410 are designed in such a manner that the pistons 452 and 454 can be brought in axial alignment with the chambers 412 and 414 and can be matingly arranged therein for coaxial telescopic movement of the container 410 and the piston unit 450 towards one another. FIG. 12 shows the prefilled telescoping multiple chamber ampoule device 400 in a closed storage position. In the closed storage position the rearward ends of the pistons 452 and 454 are inserted into the open forward ends of the chambers 432 and 434 so that the rearward end of each piston is spaced a distance from the bottom wall 415 and 417 of each one of the chambers 412 and 414 defining therein a reservoir. The reservoir defined in the chamber 412 contains a first flowable component 432, and the reservoir defined in the chamber 414 contains a second flowable component 434. In the closed storage position the peripheral sealing lips 420 are fluid-tightly pressed into circumferential contact with the outer walls of the pistons 452 and 454 at a location above the rearward end of each piston and below the transverse inlet opening 462 of the passage 460. The function of the sealing lips 420 is comparable to the function of the sealing lips 120, 220, and 320 in the first, second and third embodiment.

The optionally provided sealing lips 422 have a function comparable to that of the sealing lips 222 in the second embodiment. Preferably, the sealing lips 422 are spaced a distance from the rearward surface of the plate-like portion 419.

Furthermore, in the closed storage position the rearward end of the outer wall 455 slightly extends into the space defined by the forward portion of the outer wall 418 of the container 410 for better guiding the piston unit 450 within the container 410 during telescoping movement.

FIGS. 12 to 16 show only the two basic integrally formed parts of the prefilled ampoule device 400, i.e. the container 410 and the piston unit 450. With reference to FIGS. 5 to 11, the compartment 466 of the piston unit 450 may be utilized together with different closure and applicator means. For example, closure means such as 270, 370 or 380 may be provided, preferably, in combination with separate applicators such as 272 and 384. Closure means such as 385 may be provided with a built-in applicator 389. A built-on dropper such as 390 may be provided. In this connection, the dropper may have different forms for example a conical form ending in a dropper tip on its forward end. After telescoping movement from the closed storage position into the open release position the mixture of the two components is contained in the compartment 466 and may be dispensed via the dropper tip by pressing the dropper which is manufactured from a correspondingly flexible or elastic plastic material.

According to an alternative embodiment of the invention, instead of a common collecting and mixing compartment 366 or 466, the piston unit has at least two separate compartments integrally formed on top of the piston unit 350 or 450 for separate and successive application of the released components 332 and 334 or 432 and 434. The separate compartments may be provided by integrally forming a partition within compartment 366 or 466 dividing the single compartment into two or more separate compartments depending on the number of pistons of the piston unit. Alternatively, each one of the separate compartments may be separately formed in alignment with one of the pistons. The forward open ends of the compartments may be provided with individual closure means for each compartment or a common closure means. The closure means may be of a type as disclosed herein and may be provided with applicator means as disclosed herein.

Figure 17:
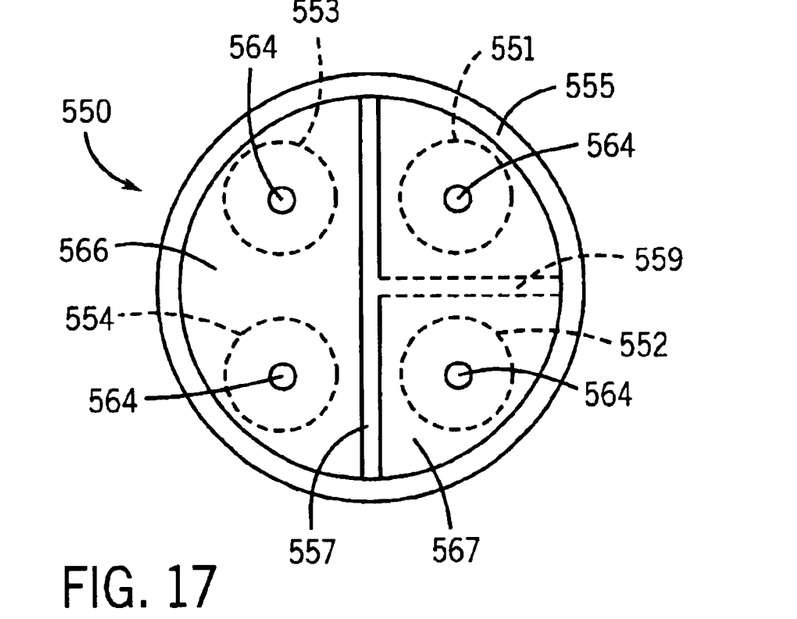
FIG. 17 is a top plan view of a piston unit of a fifth embodiment.
Figure 18:
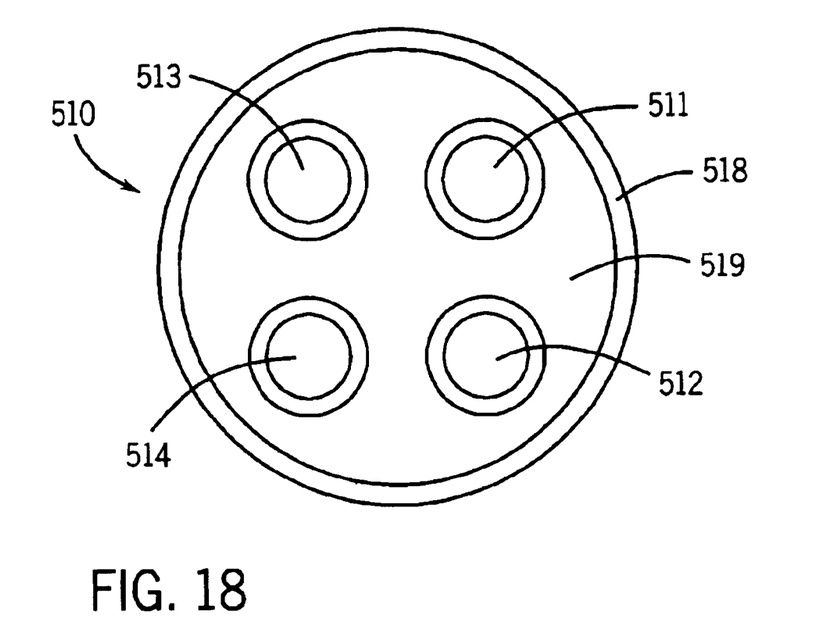
FIG. 18 is a top plan view of a container of the fifth embodiment.

Referring to FIGS. 17 and 18, a fifth embodiment of the present invention comprises an integrally formed container 510 and an integrally formed piston unit 550.

The container 510 substantially corresponds to container 410, however, includes four cylindrical chambers 511, 512, 513, 514 instead of two. The open forward ends of the chambers are integrally connected with one another by a plate-like portion 519. The piston unit 550 substantially corresponds to the piston unit 450, however, has four cylindrical plungers or pistons 551, 552, 553 and 554. The forward ends of the pistons are integrally connected to one another by means of an integrally formed connecting plate. The piston unit 550 has two integrally formed compartments 566 and 567 on top of the forward ends of the pistons. The compartments are defined by a surrounding outer wall 555 and a common partition 557. In case of need, a second partition 559 or even a third partition (not shown) may be provided in order to have more than two compartments. Providing these partitions allows to arrange one or more of the outlet openings 564 of the longitudinal passages of the pistons in common or in separate compartments. In this manner, the user can apply a mixture of two or even more components and/or selectively apply one or more components without being mixed with another component.

The device according to the invention may be used as unidose dispenser for two or more components. Standard materials for manufacturing the device according to the invention are low density polyethylenes, high density polyethylenes and polypropylenes. However, other flexible or elastic materials or elastomers may be used. This holds particularly true for the container. The piston unit may alternatively be manufactured from a rigid material, for example, a metal.

According to the invention, it is contemplated to provide prefilled telescoping multiple chamber ampoule devices which are different from the embodiments disclosed herein but operate in substantially the same manner. Therefore, it is understood that various modifications may be made to the embodiments disclosed herein. For example, three or more chambers may be provided containing either the same or different flowable media. The chambers of the container and the compartments of the piston unit may have different diameters and cross-sectional shapes. Additional annular peripheral sealing lips may be integrally formed on the inner walls of the chambers. Instead of a rather narrow sealing lip, there may be integrally provided a broader sealing ring axially extending across the transverse inlet opening of the piston in the closed storage position. While specific applicator and closure means have been described, other discharging applicators such as hollow needles, spray heads, microbrushes, brushes and the like as well as other covers such as plugs, lids and the like may be used.

I claim:

1. A prefilled telescoping multiple chamber ampoule device separately storing at least two different flowable components, comprising:

a container having at least two axially extending chambers arranged in parallel to one another, each chamber having a closed rearward end and an open forward end and a circumferential sealing lip forming an integral part of the container and projecting inwardly from an inner wall of the chamber, a piston unit having at least two axially extending pistons arranged in parallel to one another, each piston having a passage axially extending within the interior of the piston, said passage having an outlet opening at a forward end of the piston and a transverse inlet opening near a rearward end of the piston, the forward ends of the pistons being adjoined by a transversely extending mount forming an integral part of the piston unit, and each piston being in alignment with one of said chambers and being inserted, with the rearward end of the piston ahead, into the open forward end of one of said chambers and being matingly arranged therein for coaxial telescoping movement of the container and the piston unit towards one another from a closed storage position into an open release position, wherein, in the closed storage position, the rearward end of each piston is spaced a distance from the rearward end of one of said chambers so as to define therein a reservoir containing one of said components and the circumferential sealing lip is sealingly pressed into circumferential contact with an outer wall of the piston at a location between the rearward end of the piston and the transverse inlet opening of the passage of the piston so as to prevent fluid communication between the reservoir and the transverse inlet opening of the passage of the piston and prevent release of the component from the reservoir into the transverse inlet opening of the passage of the piston during transportation and storage, wherein, after initial and during telescoping movement into the open release position, the rearward ends of the pistons are moved towards the rearward ends of the chambers whereby the sealing lips expose the transverse inlet openings of the passages of the pistons to the reservoirs so as to release the components through the outlet openings of the passages of the pistons as the volumes of the reservoirs are reduced, and wherein, in both the closed storage position and the open release position, the transverse inlet opening of the passage of the piston is facing an inner wall section of the chamber that has essentially a same transverse cross-sectional area.

2. The prefilled telescoping multiple chamber ampoule device according to claim 1 wherein a chamber of said container has a further sealing lip which, in the closed storage position, is in sealing contact with the outer wall of the piston at a location between the transverse inlet opening and the forward end of the piston.

3. The prefilled telescoping multiple chamber ampoule device according to claim 1 wherein said piston unit further has a collection and mixing compartment forming an integral part of the piston unit and having a peripheral wall axially extending from a plane front face formed by the forward ends of the pistons connected by said mount in forward direction to an open forward end of the compartment in a manner that each one of the outlet openings of the passages of the pistons is in fluid communication with the compartment for simultaneously receiving each one of the released components during telescoping movement.

4. The prefilled telescoping multiple chamber ampoule device according to claim 3 further comprising a closure means which is attached to the open forward end of the compartment.

5. The prefilled telescoping multiple chamber ampoule device according to claim 4 wherein said closure means is removably attached so as to allow to dip an applicator tool into the components mixture released into the compartment.

6. The prefilled telescoping multiple chamber ampoule device according to claim 4 further comprising an elongated applicator tool extending through said closure means from the outside of the device into the compartment and being detachably connected to the closure means.

7. The prefilled telescoping multiple chamber ampoule device according to claim 3 further comprising a dropper means which is attached to the open forward end of the compartment.

8. The prefilled telescoping multiple chamber ampoule device according to claim 1 wherein said piston unit has at least two separate compartments which form integral parts of the piston unit, each compartment has a peripheral wall axially extending from a plane front face formed by the forward ends of said pistons connected by said mount in forward direction to an open forward end of the compartment in a manner that at least one of the outlet openings of the passages of the pistons is in fluid communication with the compartment for receiving at least one of the components during telescoping movement.

9. The prefilled telescoping multiple chamber ampoule device according to claim 8 further comprising closure means attached to the open forward end of the compartment.

10. The prefilled telescoping multiple chamber ampoule device according to claim 9 wherein said closure means are removably attached so as to allow to dip applicator tools into the components released into the compartments.

11. The prefilled telescoping multiple chamber ampoule device according to claim 8 further comprising elongated applicator tools extending through said closure means from the outside of the device into the compartments and being detachably connected to the closure means.

12. A prefilled telescoping multiple chamber ampoule device separately storing at least two different flowable components, comprising:

a container having at least two axially extending chambers arranged in parallel to one another, each chamber having a closed rearward end and an open forward end and an integrally formed circumferential sealing means projecting inwardly from an inner wall of the chamber, a piston unit having at least two pistons and a transversely extending mount integrally adjoining forward ends of the pistons, each piston having a passage axially extending within the interior of the piston, said passage having an outlet opening at a forward end of the piston and a transverse inlet opening near a rearward end of the piston, and each piston being in alignment with one of said chambers and being inserted, with the rearward end ahead, into the open forward end of one of said chambers and being matingly arranged therein for coaxial telescoping movement of the container and the piston unit towards one another from a closed storage position into an open release position, wherein, in the closed storage position, the rearward end of each piston is spaced a distance from the rearward end of one of said chambers so as to define therein a reservoir containing one of said components and the circumferential sealing means is sealingly pressed into circumferential contact with an outer wall of the piston at a location preventing fluid communication between the reservoir and the transverse inlet opening of the passage of the piston so as to prevent release of the component from the reservoir into the transverse inlet opening of the passage of the piston during transportation and storage, wherein, after initial and during telescoping movement into the open release position, the rearward ends of the pistons are moved towards the rearward ends of the chambers whereby the sealing means expose the transverse inlet openings of the passages of the pistons to the reservoirs so as to release the components through the outlet openings of the passages of the pistons as the volumes of the reservoirs are reduced, and wherein the container has a peripheral wall having a forward end which extends in the forward direction beyond the forward end of the piston unit so that a forward portion of the peripheral wall of the container forms a collection and mixing compartment being in fluid communication with each one of the outlet openings of the passages of the pistons for simultaneously receiving each one of the released components.

13. The prefilled telescoping multiple chamber ampoule device according to claim 12 further comprising a closure means that is attached to the open forward end of the container.

14. The prefilled telescoping multiple chamber ampoule device according to claim 13 wherein said closure means is removably attached so as to allow to dip an applicator tool into the components mixture released into the forward portion of the container.

15. The prefilled telescoping multiple chamber ampoule device according to claim 13 further comprising an elongated applicator tool extending through the closure means from the outside into the container and being detachably connected to the closure means.

16. The prefilled telescoping multiple chamber ampoule device according to claim 12 further comprising a dropper means which is attached to the forward end of the container.

17. The prefilled telescoping multiple chamber ampoule device according to claim 1 further comprising an applicator means having an axially extending rearward portion with an open rearward end, said open-ended rearward portion of said applicator means having a peripheral inside wall surrounding an open space for receiving an axially extending forward end portion of said piston unit, said forward end portion having a peripheral outside wall and a front face formed by the forward ends of the pistons connected by said mount and comprising the outlet openings of the passages of the pistons, said peripheral inside wall and said peripheral outside wall having matching cross-sectional dimensions so as to fluid-tightly attach the peripheral outside wall of the rearward end of the applicator means on the peripheral inside wall of the forward end portion of the piston unit within said space.

18. The prefilled telescoping multiple chamber ampoule device according to claim 17 wherein said applicator means comprises engagement means for manually performing telescoping movement.

19. The prefilled telescoping multiple chamber ampoule device according to claim 17 wherein the front face of the forward end portion of the piston unit defines a mixing chamber within the applicator means which has a tubular forward portion being in fluid communication with the mixing chamber.

20. The prefilled telescoping multiple chamber ampoule device according to claim 19 wherein said applicator means is a dropper means.

21. The prefilled telescoping multiple chamber ampoule device according to claim 3 wherein the collecting and mixing compartment has a transverse cross-sectional area being larger than said transverse cross-sectional area of the chamber.

22. The prefilled telescoping multiple chamber ampoule device according to claim 8 wherein the compartment has a transverse cross-sectional area being larger than said transverse cross-sectional area of the chamber.

23. The prefilled telescoping multiple chamber ampoule device according to claim 17 wherein the applicator means is made of elastic material.

24. A prefilled telescoping multiple chamber ampoule device separately storing at least two different flowable components, comprising:

a container having at least two axially extending chambers arranged in parallel to one another, each chamber having a closed rearward end and an open forward end and a circumferential sealing lip forming an integral part of the container and projecting inwardly from an inner wall of the chamber, a piston unit having at least two axially extending pistons arranged in parallel to one another, each piston having a passage axially extending within the interior of the piston, said passage having an outlet opening at a forward end of the piston and a transverse inlet opening near a rearward end of the piston, the forward ends of the pistons being adjoined by a transversely extending mount forming an integral part of the piston unit, and each piston being in alignment with one of said chambers and being inserted, with the rearward end of the piston ahead, into the open forward end of one of said chambers and being matingly arranged therein for coaxial telescoping movement of the container and the piston unit towards one another from a closed storage position into an open release position, wherein, in the closed storage position, the rearward end of each piston is spaced a distance from the rearward end of one of said chambers so as to define therein a reservoir containing one of said components and the circumferential sealing lip is sealingly pressed into circumferential contact with an outer wall of the piston at a location between the rearward end of the piston and the transverse inlet opening of the passage of the piston so as to prevent fluid communication between the reservoir and the transverse inlet opening of the passage of the piston and prevent release of the component from the reservoir into the transverse inlet opening of the passage of the piston during transportation and storage, wherein, after initial and during telescoping movement into the open release position, the rearward ends of the pistons are moved towards the rearward ends of the chambers whereby the sealing lips expose the transverse inlet openings of the passages of the pistons to the reservoirs so as to release the components through the outlet openings of the passages of the pistons as the volumes of the reservoirs are reduced, wherein, in both the closed storage position and the open release position, the transverse inlet opening of the passage of the piston is facing an inner wall section of the chamber that has essentially a same transverse cross-sectional area, and wherein said piston unit further has a collection and mixing compartment forming an integral part of the piston unit and having a peripheral wall axially extending from a plane front face formed by the forward ends of the pistons connected by said mount in forward direction to an open forward end of the compartment in a manner that each one of the outlet openings of the passages of the pistons is in fluid communication with the compartment for simultaneously receiving each one of the released components during telescoping movement.

25. A prefilled telescoping multiple chamber ampoule device separately storing at least two different flowable components, comprising:

a container having at least two axially extending chambers arranged in parallel to one another, each chamber having a closed rearward end and an open forward end and a circumferential sealing lip forming an integral part of the container and projecting inwardly from an inner wall of the chamber, a piston unit having at least two axially extending pistons arranged in parallel to one another, each piston having a passage axially extending within the interior of the piston, said passage having an outlet opening at a forward end of the piston and a transverse inlet opening near a rearward end of the piston, the forward ends of the pistons being adjoined by a transversely extending mount forming an integral part of the piston unit, and each piston being in alignment with one of said chambers and being inserted, with the rearward end of the piston ahead, into the open forward end of one of said chambers and being matingly arranged therein for coaxial telescoping movement of the container and the piston unit towards one another from a closed storage position into an open release position, wherein, in the closed storage position, the rearward end of each piston is spaced a distance from the rearward end of one of said chambers so as to define therein a reservoir containing one of said components and the circumferential sealing lip is sealingly pressed into circumferential contact with an outer wall of the piston at a location between the rearward end of the piston and the transverse inlet opening of the passage of the piston so as to prevent fluid communication between the reservoir and the transverse inlet opening of the passage of the piston and prevent release of the component from the reservoir into the transverse inlet opening of the passage of the piston during transportation and storage, wherein, after initial and during telescoping movement into the open release position, the rearward ends of the pistons are moved towards the rearward ends of the chambers whereby the sealing lips expose the transverse inlet openings of the passages of the pistons to the reservoirs so as to release the components through the outlet openings of the passages of the pistons as the volumes of the reservoirs are reduced, wherein, in both the closed storage position and the open release position, the transverse inlet opening of the passage of the piston is facing an inner wall section of the chamber that has essentially a same transverse cross-sectional area, and wherein said piston unit has at least two separate compartments which form integral parts of the piston unit, each compartment has a peripheral wall axially extending from a plane front face formed by the forward ends of said pistons connected by said mount in forward direction to an open forward end of the compartment in a manner that at least one of the outlet openings of the passages of the pistons is in fluid communication with the compartment for receiving at least one of the components during telescoping movement.

26. A prefilled telescoping multiple chamber ampoule device separately storing at least two different flowable components, comprising:

a container having at least two axially extending chambers arranged in parallel to one another, each chamber having a closed rearward end and an open forward end and a circumferential sealing lip forming an integral part of the container and projecting inwardly from an inner wall of the chamber, a piston unit having at least two axially extending pistons arranged in parallel to one another, each piston having a passage axially extending within the interior of the piston, said passage having an outlet opening at a forward end of the piston and a transverse inlet opening near a rearward end of the piston, the forward ends of the pistons being adjoined by a transversely extending mount forming an integral part of the piston unit, and each piston being in alignment with one of said chambers and being inserted, with the rearward end of the piston ahead, into the open forward end of one of said chambers and being matingly arranged therein for coaxial telescoping movement of the container and the piston unit towards one another from a closed storage position into an open release position, wherein, in the closed storage position, the rearward end of each piston is spaced a distance from the rearward end of one of said chambers so as to define therein a reservoir containing one of said components and the circumferential sealing lip is sealingly pressed into circumferential contact with an outer wall of the piston at a location between the rearward end of the piston and the transverse inlet opening of the passage of the piston so as to prevent fluid communication between the reservoir and the transverse inlet opening of the passage of the piston and prevent release of the component from the reservoir into the transverse inlet opening of the passage of the piston during transportation and storage, wherein, after initial and during telescoping movement into the open release position, the rearward ends of the pistons are moved towards the rearward ends of the chambers whereby the sealing lips expose the transverse inlet openings of the passages of the pistons to the reservoirs so as to release the components through the outlet openings of the passages of the pistons as the volumes of the reservoirs are reduced, wherein, in both the closed storage position and the open release position, the transverse inlet opening of the passage of the piston is facing an inner wall section of the chamber that has essentially a same transverse cross-sectional area, and wherein the container has a peripheral wall having a forward end which extends in the forward direction beyond the forward end of the piston unit so that a forward portion of the peripheral wall of the container forms a collection and mixing compartment being in fluid communication with each one of the outlet openings of the passages of the pistons for simultaneously receiving each one of the released components.

27. A prefilled telescoping multiple chamber ampoule device separately storing at least two different flowable components, comprising:

a container having at least two axially extending chambers arranged in parallel to one another, each chamber having a closed rearward end and an open forward end and a circumferential sealing lip forming an integral part of the container and projecting inwardly from an inner wall of the chamber, a piston unit having at least two axially extending pistons arranged in parallel to one another, each piston having a passage axially extending within the interior of the piston, said passage having an outlet opening at a forward end of the piston and a transverse inlet opening near a rearward end of the piston, the forward ends of the pistons being adjoined by a transversely extending mount forming an integral part of the piston unit, and each piston being in alignment with one of said chambers and being inserted, with the rearward end of the piston ahead, into the open forward end of one of said chambers and being matingly arranged therein for coaxial telescoping movement of the container and the piston unit towards one another from a closed storage position into an open release position, an applicator means having an axially extending rearward portion with an open rearward end, said open-ended rearward portion of said applicator means having a peripheral inside wall surrounding an open space for receiving an axially extending forward end portion of said piston unit, said forward end portion having a peripheral outside wall and a front face formed by the forward ends of the pistons and comprising the outlet openings of the passages of the pistons, said peripheral inside wail and said peripheral outside wall having matching cross-sectional dimensions so as to fluid-tightly attach the peripheral outside wall of the rearward end of the applicator means on the peripheral inside wall of the forward end portion of the piston unit within said space, wherein, in the closed storage position, the rearward end of each piston is spaced a distance from the rearward end of one of said chambers so as to define therein a reservoir containing one of said components and the circumferential sealing lip is sealingly pressed into circumferential contact with an outer wall of the piston at a location between the rearward end of the piston and the transverse inlet opening of the passage of the piston so as to prevent fluid communication between the reservoir and the transverse inlet opening of the passage of the piston and prevent release of the component from the reservoir into the transverse inlet opening of the passage of the piston during transportation and storage, wherein, after initial and during telescoping movement into the open release position, the rearward ends of the pistons are moved towards the rearward ends of the chambers whereby the sealing lips expose the transverse inlet openings of the passages of the pistons to the reservoirs so as to release the components through the outlet openings of the passages of the pistons as the volumes of the reservoirs are reduced, and wherein, in both the closed storage position and the open release position, the transverse inlet opening of the passage of the piston is facing an inner wall section of the chamber that has essentially a same transverse cross-sectional area.

\* \* \* \* \*

UNITED STATES PATENT AND TRADEMARK OFFICE
CERTIFICATE OF CORRECTION

PATENT NO. : 6,719,729 B2
DATED : April 13, 2004
INVENTOR(S) : Alberto C. Sogaro It is certified that error appears in the above-identified patent and that said Letters Patent is hereby corrected as shown below:

<u>Column 19,</u>
Line 31, "wail" should be -- wall --.

Signed and Sealed this

Tenth Day of August, 2004

JON W. DUDAS
*Acting Director of the United States Patent and Trademark Office*